(12) United States Patent
Moser et al.

(10) Patent No.: US 7,455,874 B2
(45) Date of Patent: Nov. 25, 2008

(54) METHOD FOR THE FABRICATION OF A BIOSENSOR COMPRISING AN ENZYME ELECTRODE ARRANGEMENT

(75) Inventors: Isabella Moser, Hebelstrasse 6, 79356 Eichstetten (DE); Gerald A. Urban, Freiburg (DE); Anastasia Zacharopoulou, Pireas (GR); Panagiota S. Petrou, Kapandriti (GR)

(73) Assignee: Isabella Moser, Eichstetten (DE)

( * ) Notice: Subject to any disclaimer, the term of this patent is extended or adjusted under 35 U.S.C. 154(b) by 823 days.

(21) Appl. No.: 10/987,671

(22) Filed: Nov. 12, 2004

(65) Prior Publication Data
US 2005/0205422 A1    Sep. 22, 2005

Related U.S. Application Data

(63) Continuation of application No. PCT/EP03/04832, filed on May 8, 2003.

(51) Int. Cl.
| | |
|---|---|
| *G01N 3/00* | (2006.01) |
| *G01N 27/327* | (2006.01) |
| *H01B 13/00* | (2006.01) |
| *B32B 3/26* | (2006.01) |

(52) U.S. Cl. .................. 427/2.13; 427/2.11; 216/13; 264/134; 204/403.01

(58) Field of Classification Search ............... 204/403.01–403.15; 205/777.5, 778, 792; 427/2.11, 427/2.13; 216/13; 264/134
See application file for complete search history.

(56) References Cited

U.S. PATENT DOCUMENTS

| | | | | |
|---|---|---|---|---|
| 4,894,137 A | * | 1/1990 | Takizawa et al. | 204/403.09 |
| 4,897,173 A | * | 1/1990 | Nankai et al. | 204/403.05 |
| 6,875,327 B1 | * | 4/2005 | Miyazaki et al. | 204/403.14 |
| 2004/0106166 A1 | | 6/2004 | Matsumoto | |

FOREIGN PATENT DOCUMENTS

| | | |
|---|---|---|
| DE | 4128569 C1 | 12/1992 |
| DE | 4208186 A1 | 9/1993 |
| DE | 689 13 144 T2 | 5/1994 |
| DE | 10025174 A1 | 12/2001 |
| EP | 0 264 210 A2 | 4/1988 |
| JP | 52 139778 | 11/1977 |
| JP | 02087056 A | 3/1990 |

(Continued)

OTHER PUBLICATIONS

Mădăraş et al., Miniaturized Biosensors Employing Electropoloymerized permselective Films and Their Use for Creatinine assays in Human Serum, Anal. Chem. 1996, 68, 3832-3839.*

(Continued)

*Primary Examiner*—Alex Noguerola
(74) *Attorney, Agent, or Firm*—Renner, Otto, Boisselle & Sklar, LLP

(57) ABSTRACT

The present invention relates to an enzyme electrode arrangement comprising a substrate with a surface roughness in the range of 20 nm to 10 microns, a metal electrode, an ultrathin semipermeable membrane with a thickness in the range of 10-100 nm and at least one enzyme membrane, a method for the fabrication of such arrangement and a biosensor arrangement comprising such electrode arrangement.

23 Claims, 3 Drawing Sheets

FOREIGN PATENT DOCUMENTS

| | | |
|---|---|---|
| JP | 02099850 A | 4/1990 |
| JP | 03130656 A | 6/1991 |
| JP | XP-002253972 | 9/2003 |
| WO | WO 03/010529 A1 | 2/2003 |

OTHER PUBLICATIONS

Nakamura et al. ed., Immunochemical Assays and Biosensor Technology for the 1990s, ASM Press, 1992, p. 347.*

Urban et al., Performance of integrated glucose and lactate thin-film microbiosensors for clinical analysers, Sensors and Actuators, B, 18-19 (1994) 592-596.*

Boedeker Plastics Kapton specification datasheet, downloaded Apr. 15, 2008.*

Geise et al., Electropolymerized Films to Prevent interferences and Electrode Fouling in Biosensors, Biosensors & Bioelectronics 6 (1991) 151-160.*

Cosofret et al., Microfabricated Sensor arrays Sensitive to pH and K+ for Ionic Distribution measurements in the Beating Heart, Anal. Chem. 1995, 67, 1647-153.*

PCT Search Report dated Sep. 24, 2003.

* cited by examiner

METHOD FOR THE FABRICATION OF A BIOSENSOR COMPRISING AN ENZYME ELECTRODE ARRANGEMENT

CROSS-REFERENCE TO RELATED APPLICATIONS

This application is a continuation of co-pending PCT patent application No. PCT/EP03/04832, filed 8 May 2003, which claims the benefit of German patent application serial number 102 21 435.2-52, filed 14 May 2002. Each of the aforementioned related patent applications is herein incorporated by reference in their entireties.

BACKGROUND OF THE INVENTION

1. Field of the Invention

The present invention relates to an enzyme electrode arrangement.

2. Description of the Related Art

Biomolecule detection is of key importance in pharmaceutical research and clinical diagnostics. Typically, this detection is performed utilizing a so called affinity reaction where complementary analytes bind together specifically. Fundamentally, there is the problem of detecting the smallest concentrations available in one test. Mostly, today's measurement systems sensitivities are too small to directly detect these low concentrations. Therefore, amplification schemes amplifying indirectly the signal as much as possible above the lower limit of detection of the measurement system are used.

Affinity sensors are a special type of biosensors utilizing any type of biomolecular recognition of highly specific affinity partners as e.g. antibody-antigen, nucleic acid-complementary nucleic acid, or receptor-ligand. In general bio- and affinity sensors are composed of two components: the biological component for the specific recognition of an analyte and the detector component, the so called transducer that should capture this biomolecular reaction and transform it into an analyzable signal. The selective biological components (e.g. nucleic acids, enzymes, antibodies, antigens or micro organisms) are intimately immobilized to the transducer and nowadays can be detected with a broad range of measurement principles. The choice of the transducer is governed by the reaction of the biological component and the resulting changes. The state of the art describes many transducers working on different principles. Common transducers are working on electrochemical, electrical or optical principles.

Sensitivity and specificity of the biomolecular recognition indicate—amongst other parameters like reproducibility, manufacturing costs, usability—the quality and practical usability of the sensor. The specificity of the biosensors is largely made-up by the biological component. One specific bioactive material at a time is used to detect the searched substance out of many others—also similar ones. The chemical reactions thereby taking place influence physical parameters, for example the electrical potential. The basic values or their changes respectively are transformed by the transducer in an electrical output signal that becomes subsequently electronically amplified. As a result, the biological component of the sensor, e.g. an enzyme, a receptor, or an antibody, binds the substance to be analyzed—essentially only this one—and generates a signal whose intensity is proportional to the concentration of the substance bound. For example, using enzymes the generation of a reaction product can generate an electrical signal that is picked up by an electrode. In the case of an enzyme sensor for the determination of glucose, the electrode is typically covered with a thin membrane comprising the immobilized glucose oxidase (GOD). The enzyme molecules are, e.g., entrapped in gelatin or polyurethane. The membrane is permeable only for molecules of a particular size. Out of a mixture of amino acids, proteins, fats, glucose, and other sugars the enzyme GOD converts only the glucose, also consuming oxygen. Glucono-lactone and hydrogen peroxide is formed. The immobilized enzyme is not washed out of the membrane but can be reused until its natural aging. In contrast, the smaller molecules like glucose, hydrogen peroxide and oxygen easily enter the membrane from the solution to be analyzed and vice versa. The hydrogen peroxide generated in the enzymatic reaction, as an electro active substance, donates two electrons per molecule to the electrode. The electrons generated in this reaction are subsequently delivered to the biosensors electrode—generating a microcurrent. Simultaneously to the reaction of the glucose with the enzyme GOD, sometimes on a bio-inactive field, a blank current is measured that can be generated by interfering substances in the blood sample. Such interfering substances can be for example drugs, vitamins, or metabolic products in high concentrations that can also generate a micro-current. The net-current calculated in this way is a measure for the amount of glucose in e.g. a blood sample and can be converted into a proportional blood glucose concentration.

Difficulties still pose problems such as being reproducible, simple to use, and stable immobilization of the biological component. For example, to obtain a fast response time and a reliable reading a thin layer of immobilized bio-molecule is desirable and shelf life and operational stability demand a high value of immobilized enzymatic activity. Adsorption to adequate surfaces including a metal electrode layer yields relatively unstable systems. The associated problems are aggravated with planar systems or carriers respectively, insofar as a basically mechanical sandwich set-up for making of a sensor can not be used anymore. In case of loss of the mechanical integrity of such sandwich type biosensors due to cracks formed in the individual membrane layers, the resulting readings are falsified due to the above mentioned interfering substances to an extent that even the above mentioned differential measurement method using a bio-inactive field cannot compensate.

Therefore, the object underlying the present invention is to provide a stable enzyme electrode arrangement or biosensors respectively, made in a sandwich set-up, in order to enable fast and highly precise measurements without the influence of interferences during continuous use and in this way provide a reliable signal amplification of biological binding reactions. This can be realized without covalent coupling of the biological component typically immobilized within a membrane.

SUMMARY OF THE INVENTION

The present invention relates to an enzyme electrode arrangement comprising a substrate with a surface roughness in the range of 20 nm to 10 microns, a metal electrode, an ultrathin semipermeable membrane with a thickness in the range of 10-100 nm and at least one enzyme membrane, a method for the fabrication of such arrangement and a biosensor arrangement comprising such electrode arrangement. In particular, there is provided an enzyme electrode arrangement comprising in the following order at least one substrate with a surface roughness in the range of 20 nm to 10 microns, determined by AFM measurement, a metal electrode, an ultrathin semipermeable membrane with a thickness in the range of 10 to 100 nm, and at least one enzyme membrane.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1A:
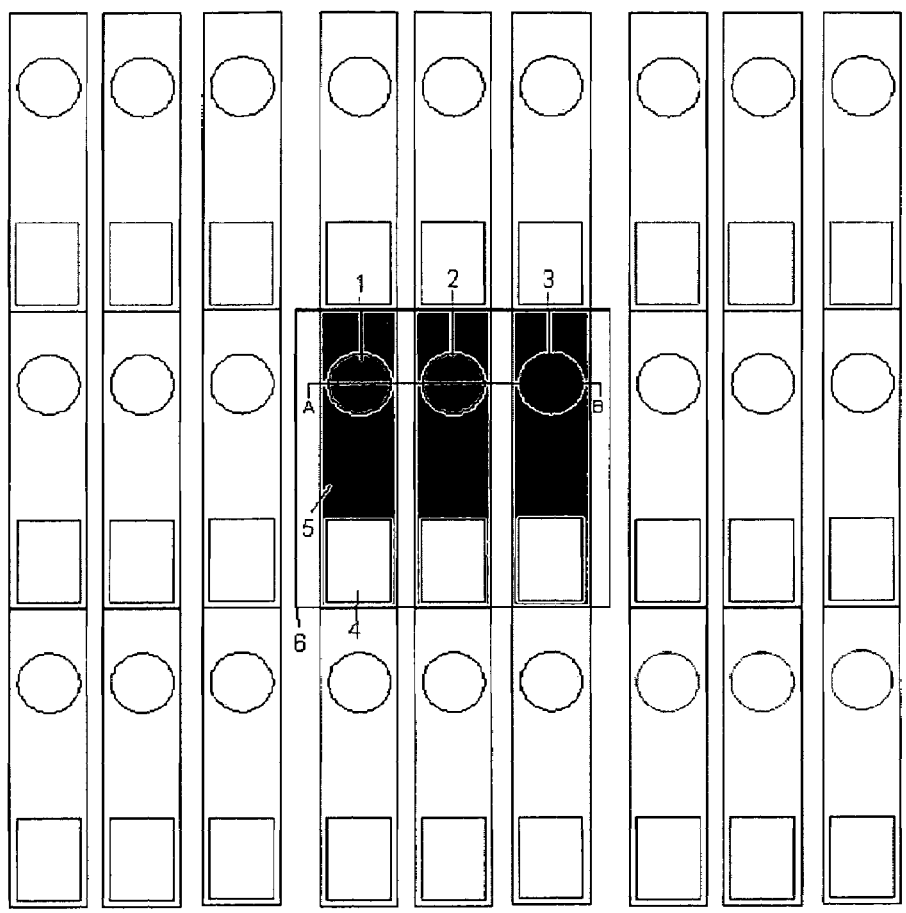
FIG. 1 shows a schematic top view (FIG. 1a) of a section of an exemplary biosensor arrangement according to the present invention and a cross-section along the line A-B (FIG. 1b).

The material of the substrate is not subjected to any specific limitation as long as it is able to provide a surface roughness in the range of 20 nm to 10 microns and is generally suited as a carrier material for biosensors. Preferably, the material comprises an organic polymer, selected from the group of polyacrylate-, polyimide-, polyester-, and polycarbonate-homo- and copolymers of them. Alternatively, substrates on the basis of inorganic materials as for example porous silicon or etched glass can be used. Preferably, the substrates used have a thickness in the range of 0.01 to 5.0 mm.

The metal electrode can be made from any material typically used for biosensors, as e.g. platinum or gold. The layer thickness of the metal electrode is chosen thin enough to allow the layer to fit to the surface roughness structure of the micro rough substrate. In particular, the metal electrode layer is thin enough to conserve or take over at least a part of the surface roughness of the substrate used according to the present invention on the metal surface. A metal electrode for an enzyme electrode arrangement according to the present invention usually has a layer thickness in the range of 50 to 250 nm.

According to the sandwich style construction of the enzyme electrode arrangement according to the present invention an ultrathin semipermeable membrane or an anti-interference membrane respectively is placed on top of the metal electrode. In the course of the present invention, this refers to a membrane having sufficient porosity to allow the diffusion of molecules like $H_2O_2$ or $O_2$ or those of similar size to the metal electrode. The access of substances like e.g. ascorbic acid, uric acid, acetaminophen, and gentisic acid as a metabolite of acetyl salicylic acid, each of them having a molecular weight higher than 100 Dalton, and, if they could access the metal electrode, would become oxidized to cause a "wrong" signal, is prevented by the ultrathin semipermeable membrane. This semipermeable membrane is preferably made from an organic polymeric material made by electro polymerization of organic monomers chosen from (i) diamino-, (ii) dihydroxy- or (iii) both amino- and hydroxy-substituted aromatic hydrocarbons and mixtures of them. The organic monomers are chosen preferably from 1,2-diaminobenzene, 1,3-diaminobenzene, 2,3-diaminonaphthaline, 1,5-diaminonaphthaline, 1,8-diaminonaphthaline, 5-amino-1-naphthol or resorcin.

On top of the semi-permeable membrane, a usual enzyme membrane is placed. Preferably, at least one enzyme from the group of the oxidases is immobilized. The oxidases can be chosen from the group consisting of lactate oxidase, galactose oxidase, L-2-hydroxycarbonic acid oxidase, glucose oxidase, glycolate oxidase, hexose oxidase, L-gulonolactone oxidase, L-sorbose oxidase, pyridoxol-4-oxidase and alcohol oxidase.

Within the sandwich composite in the enzyme electrode arrangement according to the present invention, a simple mechanical self-cohesion is generated due to the micro roughness transferred from the micro rough substrate via the metal electrode and the semipermeable membrane to the lower surface side of the enzyme membrane, enabling the fast and highly precise measurement of the respective analytes without the occurrence of interference effects during prolonged use, especially advantageous without covalent coupling of the biological components usually immobilized in a membrane. In this way, the decline of the anti-interference effect with time, as occurring with flat substrates, is advantageously counteracted.

Additionally, to further improve the measurement accuracy, a diffusion limiting membrane, e.g. a pHEMA-membrane, and/or a catalase-membrane can be placed on top of this enzyme membrane to prevent or minimize disturbing effects.

A further aspect of the present invention relates to a method for the fabrication of an enzyme electrode arrangement, comprising the steps of:
(a) providing a substrate with a surface roughness in the range of 20 nm to 10 microns,
(b) depositing a metal electrode layer on top of the substrate in a layer thickness sufficiently thin to take over the surface roughness structure of the substrate,
(c) depositing a semipermeable membrane in a thickness in the range of 10 to 100 nm, and
(d) depositing at least one enzyme membrane.

The creation of the surface roughness on the substrate can in particular be made by providing a pretreated metallic or ceramic master and subsequent replication by application of a respective liquid or thermoplastic polymer precursor or polymer respectively and subsequent curing or cooling or also by thermal embossing to the polymer precursor or polymer respectively, providing a substrate with a surface roughness in the range of 20 nm to 10 microns. In order to provide the respective micro rough surface serving as the negative mould in this replication process, this master can be preprocessed e.g. by micro-milling, photolithographical etching, sand blasting, mechanical imprinting, or galvanic roughening. After the substrate is embossed in the master, the substrate is separated from the master either mechanically or e.g. by dissolving the master in an etch process.

A further embodiment with regard to the generation of the surface roughness of the substrate utilizes etching of the substrate. Thus, for example, glass surfaces can be exposed in the known way to an atmosphere of hydrofluoric acid. Moreover, for example, polyimide can be etched with mixtures of acids usually used in the state of the art.

The deposition of the metal electrode layer in step (b), in particular platinum or gold electrodes, can be done by, e.g., using vacuum deposition processes, for example PVD- or CVD-processes. The metal electrode is deposited in such a thickness matching the requirement to take over the micro roughness of the substrate. The film thickness of the metal electrode layer is chosen so that at least a part of the surface roughness of the substrate according to the present invention is retained or taken over respectively. Usually, the metal electrode according to the present invention has a layer thickness in the range of 50 to 250 nm.

Preferably, the semipermeable membrane deposited in step (c) is made by electro polymerization from organic monomers selected from diamino- or dihydroxy-substituted benzene derivatives or naphthalene derivatives and mixtures of them, in the usual manner. For example, the deposition can be done by electro polymerization by means of a cyclic variation of the potential in a solution of, e.g., neutral phosphate buffer.

The deposition of the membrane precursor solutions for the formation of the enzyme membranes and if necessary one or more further membranes, as e.g. a diffusion limiting membrane or a catalase membrane, can be done by conventional processes like, e.g., dispensing or spin/dip-coating. In the course of the present invention, at first, a photo reactive membrane precursor solution is usually deposited that is subsequently cross linked by exposure to UV light under oxygen exclusion, e.g., in an argon atmosphere. Preferably, the enzyme membrane solutions contain at least one enzyme from the group of the oxidases. The oxidases can be chosen from the group consisting of lactate oxidase, galactose oxidase, L-2-hydroxycarbonic acid oxidase, glucose oxidase, glycolate oxidase, hexose oxidase, L-gulonolactone oxidase, L-sorbose oxidase, pyridoxol-4-oxidase and alcohol oxidase. A typical membrane-precursor-solution contains pHEMA (poly-hydroxyethylacrylate) as polymeric binder, HEMA (hydroxyethylmethacrylate) as reactive monomer, TEGDMA (tetraethyleneglycoldimethacrylate) as cross linker, polyethylene glycole as plasticizer, and a photo initiator like e.g. ω,ω'-dimethoxy-ω-phenylacetophenone and water. After dissolution of the aforementioned components and filtration the desired enzymes are added to the precursor solution.

Preferably, such enzymes are immobilized in a cross linked pHEMA membrane on the enzyme electrode arrangement according to the present invention.

In the immobilization of proteins, as e.g. enzymes, within polymers by means of polymerizing or cross linking them respectively, initiated by free radicals, generated in particular by means of photolysis using UV-light, proteins containing sulfhydryl(—SH)-groups on their surface pose the problem that such —SH groups consume free radicals to such an extent that the polymerization or cross liking respectively becomes significantly inhibited. According to the present invention, this can be avoided by adding a molecular quinoid agent that is capable of abstracting a hydrogen atom from said —SH groups under UV light exposure, to the composition for the fabrication of an enzyme membrane. As a result, not only the consumption of other radicals by the —SH groups is avoided, but additionally the sulfur radical intermediate as formed supports the polymerization or cross linking respectively to be carried out for the formation of the enzyme membrane. Examples of molecular chinoid agents include un-substituted or substituted benzoquinones, anthraquinones or naphthoquinones and their derivatives or a mixture of one or more of them can be used. Derivatives of the aforementioned compounds for example imine-, oxime-, cyanimine- and/or dicyanmethide compounds, as e.g. 1,4-benzoquinone dioxime, 1,4-benzoquinone diimine, tetracyano-p-quinodimethane and N,N'-dicyanoquinone diimine can be used. Preferably, an un-substituted or substituted, ortho- or para-benzoquinone is used as molecular quinoid agent in the electrode formulation according to the present invention. Besides linear or branched ($C_1$-$C_6$)-alkyl-, ($C_3$-$C_7$)-cycloalkyl-, ($C_1$-$C_6$)-alkoxy-und ($C_1$-$C_6$)-thioether residues, the substituents can also be one or more, identical or different electron attracting groups, preferably selected from fluorine, chlorine, bromine, nitro, cyano and sulfonate. As such, quinoid agents for example chloranil, duroquinone and p-benzoquinone can be used.

Preferably, the deposition of the membrane solutions is done by dispensing, whereas the cannula used for dispensing, if necessary, can be coated with a hydrophobic layer such that both the stability of the dispensing process and its reproducibility is improved. The deposition of the active membranes by means of dispensing is especially favorable if instead of a single, accordingly big electrode, a multiplicity of smaller electrodes is provided to realize the desired signal intensity according to the present invention.

A further aspect of the present invention relates to the use of the enzyme electrode arrangement according to the present invention in a biosensor arrangement. Such a biosensor arrangement, beside the enzyme electrode arrangement according to the present invention where the metal electrode acts as working electrode, can additionally comprise a Ag/AgCl-electrode as a reference electrode and/or a difference measurement electrode or "dummy-electrode" respectively for the elimination of side effects by means of difference measurement. Preferably, the reference electrode and/or the difference measurement electrode are placed on the same micro rough substrate material, as intended for the enzyme electrode arrangement according to the present invention, i.e., the reference electrode and/or the difference measurement electrode are arranged in predefined spatial neighborhood to the enzyme electrode arrangement comprising the enzyme membrane according to the present invention.

In order to insulate the biosensor arrangement and to provide submersions for the accommodation of the enzyme membrane or the reference electrode and/or the difference measurement electrode respectively, a 25 to 200 micron thick layer of a photo patternable material, e.g. Vacrel® 8120, supplied by DuPont, can be provided for the biosensor arrangement according to the present invention. The application of such layer also to the back side of the substrate, that is the carrier of the biosensor arrangement according to the present invention, can compensate for the occurrence of mechanical stress that otherwise could cause bending, also enabling the use of very thin substrate materials in the course of the present invention.

To provide a seal or spacer surrounding the desired measurement chamber, the use of a 25 to 200 micron thick photo patternable material can be provided. Moreover, a double sided patterned adhesive foil can be used for the connection of the sensor and a top part, where such an adhesive foil can simultaneously serve as a spacer and seal for the formation of a measurement chamber with the sensor electrodes. A patterned stainless steel foil can be used as the top part of such a measurement chamber, whereby such a stainless steel foil serves both for enclosing the measurement chamber and for draining the current of the sensor.

Figure 1B:
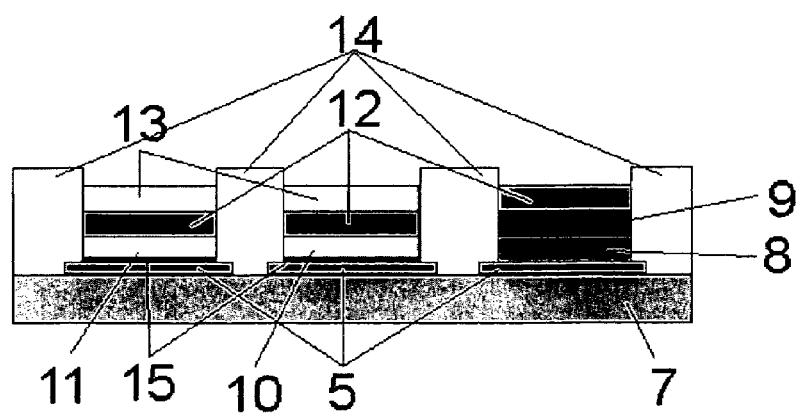

FIG. 1 shows a schematic top view of such an exemplary biosensor arrangement according to the present invention, where an enzyme electrode (1) according to the present invention, a dummy-electrode (2) and a Ag/AgCl-reference electrode (3) are spatially separated from each other on a chip surface (6), as e.g. a polyimide foil, are placed. The numbers (4) or (5) respectively represent the respective contact areas (contact pads) or metal surfaces like the metal electrode layer respectively. At the contact pads, electrical connections (not shown) are arranged that usually lead to one or more measurement instruments. FIG. 1b shows schematically a cross sectional view along the line A-B. On the substrate (7) beside an enzyme electrode built from the metal electrode layer (5), the semipermeable membrane (15), the enzyme membrane (11), a diffusion limiting membrane (12) and a catalase-membrane (13), a dummy-electrode with a dummy-membrane or a difference sensor membrane respectively (10) instead of the enzyme membrane and a Ag/AgCl-electrode ((8) and (9) respectively denote Ag and AgCl respectively) are arranged. The electrodes (1), (2) and (3) and the contact areas are arranged in the openings of the insulation layer, typically made from a photo patternable dry film resist, covering the substrate (7).

Figure 2A:
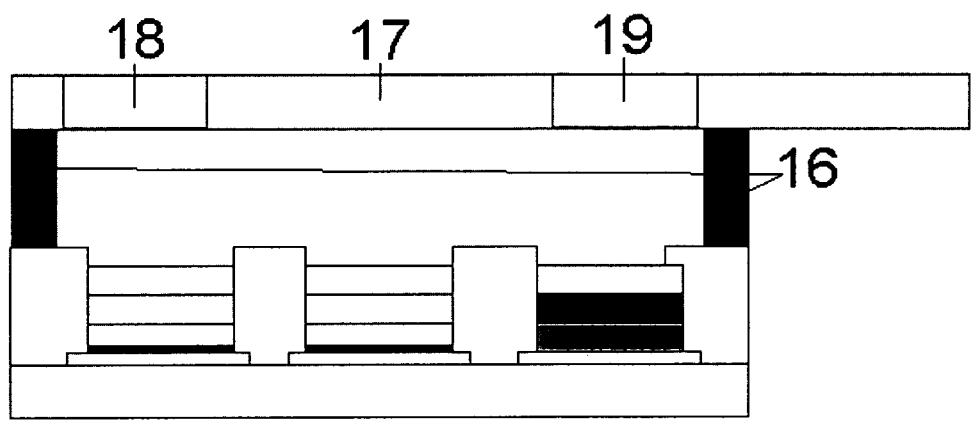
FIG. 2 shows a schematic cross-section (FIG. 2a) of an exemplary biosensor arrangement according to the present invention in combination with a flow through cell and a respective top view (FIG. 2b).
Figure 2B:
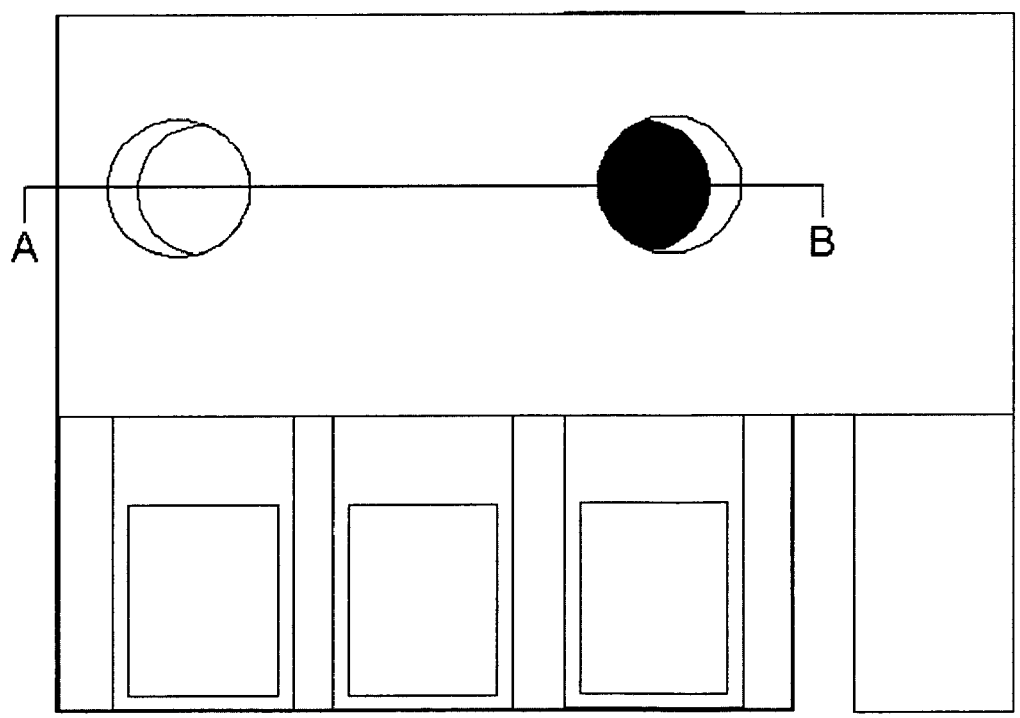

FIG. 2 shows schematically a cross section (FIG. 2a) of an exemplary biosensor arrangement according to the present invention in combination with a flow through cell and a corresponding top view (FIG. 2b). The flow through cell is sealed against the outside by a second layer or dry film resist (16). Alternatively, a double sided patterned adhesive foil can be used for this purpose. As a top part of the flow cell, a patterned stainless steel foil (17) is used. The notations (18) and (19) denote a fluid inlet and outlet respectively.

Figure 3:
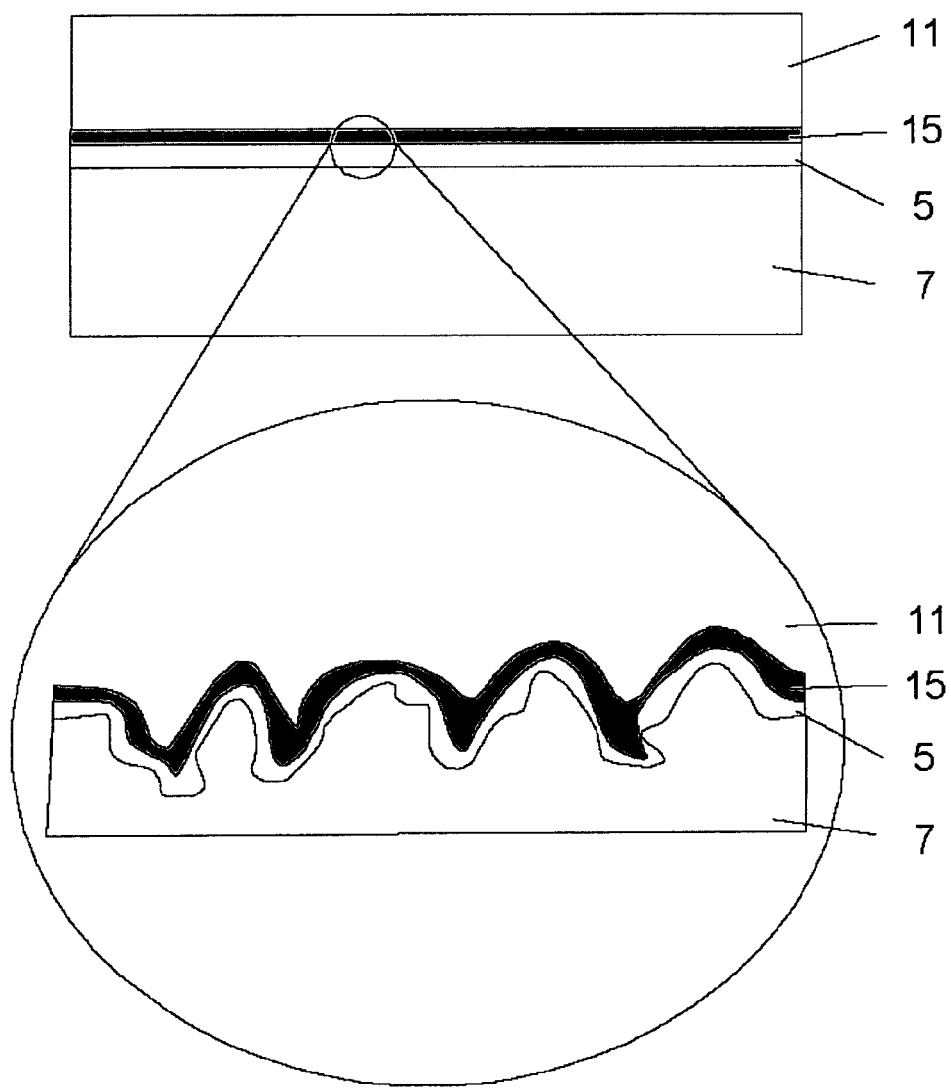
FIG. 3 shows a schematic cross-section of the layer set-up of an enzyme electrode arrangement according to the present invention and a magnified section out of it.

FIG. 3 shows schematically a cross sectional view of the layered sandwich construction of an enzyme electrode arrangement according to the present invention and a magnification from it. On a micro rough substrate (7) according to the present invention, a metal electrode (5) is placed in a layer thickness accordingly thin to take over the surface roughness structure of the substrate. On top of this metal electrode layer, an ultrathin semipermeable membrane (15) is placed, on top of which an enzyme membrane (11) is placed.

The present invention is exemplified in more detail in the following example.

EXAMPLE

For the realization of a biosensor arrangement according to the present invention, first, the copper layer was removed from a commercially available polyimide foil (Pyralux® AP, DuPont) by etching with 20 wt.-% $Na_2S_2O_8$, whereby a polyimide substrate with a micro rough surface was obtained. Successively, a commercially available photo resist layer (Tentmaster™ 100, DuPont) was applied on the micro rough substrate obtained in such a way and photo lithographically patterned to form predefined zones or contact areas respectively e.g. for the application of the analyte.

Successively, a 100 nm thick layer of platinum was deposited in a vacuum evaporation process for the formation of a metal electrode layer. In order to avoid surface contaminations of the platinum metal electrode layer fabricated in such a way in the subsequent processing steps, if necessary, a 100 nm thick titanium layer can be deposited onto the platinum layer. After removal of the resist layer as previously applied, a patterned metal layer remained on the polyimide substrate.

In order to compensate for the shrinkage and for the purpose of insulation of such a patterned polyimide substrate, dry film resist layers (Vacrel® 8120, DuPont) were applied to top and bottom sides and again photo lithographically patterned.

After removal of the titanium layer by conventional etching, a Ag/AgCl-reference electrode was made by galvanic deposition of a silver layer and subsequent transformation of a part of it into silver chloride in a galvanic process in a 0.1 M solution of KCl.

Subsequently, a semipermeable membrane was deposited by means of electro polymerization of a solution of 3 mM 1,3-diaminobenzene in neutral phosphate buffer by cyclic variation of the potential over 18 hours.

Next, a glucose oxidase-containing membrane based on the following composition was applied:
1 vol.-part of a solution C+1 vol.-part of a solution B+6 vol.-parts of a solution A, whereby solutions A, B and C have the following compositions:
Solution A: 24 wt.-% pHEMA, 12 wt.-% HEMA, 3 wt.-% TEGDMA, 1 wt.-% ω,ω'-dimethoxy-ω-phenyl acetophenone, 36 wt.-% PEG400 und 24 wt.-% H2O;
Solution B: 0.2 wt.-% benzoquinone and 1 wt.-% N-methyidiethanolamine in PEG 400;
Solution C: 25 wt.-% glucose oxidase-lyophilisate in water Subsequently a membrane was applied on a "dummy" electrode that had been additionally arranged on the substrate, whereby this "dummy" membrane was based on the following composition: 1 vol.-part water+1 vol.-part solution B+6 vol.-parts of the aforementioned solution A.

In order to slow down the diffusional matter access, additionally a diffusion limiting membrane based on the following composition was applied on the enzyme membrane made before:
18 wt.-% pHEMA, 18 wt.-% HEMA, 3 wt.-% TEGDMA, 1 wt.-% ω,ω'-dimethoxy-ω-phenylacetophenone, 36 wt.-% PEG400 und 24 wt.-% H2O Finally, a catalase membrane was applied in order to prevent sensor cross talk and to minimize the dependency of sensor sensitivity on fluid convection. The catalase-membrane was based on the following composition:
1 vol.-part of a solution D+1 vol.-part glycerol+6 vol.-parts of a solution A, whereby solution A had the aforementioned composition and solution D was composed as following:
Solution D: 25 wt.-% catalase-lyophilisate in water.

While the foregoing is directed to embodiments of the present invention, other and further embodiments of the invention may be devised without departing from the basic scope thereof, and the scope thereof is determined by the claims that follow.

What is claimed is:

1. A method of producing an enzyme electrode arrangement, comprising:
providing a substrate with a surface roughness in the range of 10 nm to 10 microns;
depositing a metal electrode layer onto the substrate;
depositing a semipermeable membrane in a thickness in the range of 10 nm to 100 nm; and
depositing at least one enzyme membrane;
wherein the method further comprises creating the surface roughness by providing a preprocessed master and subsequent replication by application of a fluid polymer precursor to the master and curing of the polymer precursor to provide the substrate with the surface roughness in the range of 20 nm to 10 microns.

2. The method of claim 1, wherein the substrate is made from an organic polymer selected from the group consisting of polyacrylate-, polyimide-, polyester-, and polycarbonate-homo- and copolymers.

3. The method of claim 1, wherein the metal electrode has a layer thickness in a range of 50 nm to 250 nm.

4. The method of claim 3, wherein the metal electrode is selected from the group consisting of a platinum electrode and a gold electrode.

5. The method of claim 1, wherein the enzyme membrane contains at least one enzyme from the group of oxidases.

6. The method of claim 5, whereby the oxidases are chosen from the group consisting of lactate oxidase, galactose oxidase, L-2-hydroxycarbonic acid oxidase, glucose oxidase, glycolate oxidase, hexose oxidase, L-gulonolactone oxidase, L-sorbose oxidase, pyridoxol-4-oxidase and alcohol oxidase.

7. The method of claim 1, further comprising incorporating the enzyme electrode arrangement into a biosensor arrangement.

8. The method of claim 1, wherein the master is preprocessed by a process selected from the group consisting of micro milling, photo lithographical etching, sand blasting, mechanical imprinting and galvanic roughening.

9. The method of claim 1, wherein depositing the metal electrode layer is carried out by using a vacuum deposition process.

10. The method of claim 1, wherein depositing the semipermeable membrane is by electro polymerization of organic monomers selected from the group consisting of diamino-, dihydroxy-, both amino- and hydroxy- substituted aromatic hydrocarbons and their mixtures.

11. The method of claim 1, wherein depositing the at least one enzyme membrane is carried out by dispensing.

12. The method of claim 1, wherein depositing the at least one enzyme membrane includes dispensing a photo reactive membrane-precursor solution that is subsequently cross linked by exposure to UV light in an oxygen free atmosphere.

13. A method of producing an enzyme electrode arrangement, comprising:
    providing a substrate with a surface roughness in the range of 10 nm to 10 microns;
    depositing a metal electrode layer onto the substrate;
    depositing a semipermeable membrane in a thickness in the range of 10 nm to 100 nm; and
    depositing at least one enzyme membrane;
    wherein the method further comprises generating the surface roughness in the substrate by removal of a metal from a metal-polymer laminate foil by etching.

14. The method of claim 13, wherein the substrate is made from an organic polymer selected from the group consisting of polyacrylate-, polyimide-, polyester-, and polycarbonate-homo- and copolymers.

15. The method of claim 13, wherein the metal electrode has a layer thickness in a range of 50 nm to 250 nm.

16. The method of claim 13, wherein the metal electrode is selected from the group consisting of a platinum electrode and a gold electrode.

17. The method of claim 13, wherein the enzyme membrane contains at least one enzyme from the group of oxidases.

18. The method of claim 17, whereby the oxidases are chosen from the group consisting of lactate oxidase, galactose oxidase, L-2-hydroxycarbonic acid oxidase, glucose oxidase, glycolate oxidase, hexose oxidase, L-gulonolactone oxidase, L-sorbose oxidase, pyridoxol-4-oxidase and alcohol oxidase.

19. The method of claim 13, further comprising incorporating the enzyme electrode arrangement into a biosensor arrangement.

20. The method of claim 13, wherein depositing the metal electrode layer is carried out by using a vacuum deposition process.

21. The method of claim 13, wherein depositing the semipermeable membrane is by electro polymerization of organic monomers selected from the group consisting of diamino-, dihydroxy-, both amino- and hydroxy- substituted aromatic hydrocarbons and their mixtures.

22. The method of claim 13, wherein depositing the at least one enzyme membrane is carried out by dispensing.

23. The method of claim 13, wherein depositing the at least one enzyme membrane includes dispensing a photo reactive membrane-precursor solution that is subsequently cross linked by exposure to UV light in an oxygen free atmosphere.

* * * * *